US00PP08371P

United States Patent [19]

Fruehwirth

[11] Patent Number: Plant 8,371

[45] Date of Patent: Sep. 14, 1993

[54] POINSETTIA PLANT NAMED 529

[75] Inventor: Franz Fruehwirth, Encinitas, Calif.

[73] Assignee: Paul Ecke Ranch, Inc., Encinitas, Calif.

[21] Appl. No.: 730,348

[22] Filed: Jul. 15, 1991

[51] Int. Cl.[5] ..... A01H 5/00

[52] U.S. Cl. ..... Plt./86.4

[58] Field of Search ..... Plt./86.1–86.4

[56] References Cited

U.S. PATENT DOCUMENTS

P.P. 6,694 3/1989 Ecke ..... Plt. 86.1

*Primary Examiner*—James R. Feyrer

*Attorney, Agent, or Firm*—Arnold, White & Durkee

[57] ABSTRACT

Poinsettia '529' is an early flowering cultivar with dark red flower bracts. It has dark green, medium size foliage, stiff stems and a strong branching habit. Cultivar '529' has traits which differ from 'Lilo' (U.S. Plant Pat. No. 6,694) and make '529' a more desirable plant for commercial pot plant production. Namely, cultivar '529' is earlier flowering, shorter, stiffer stemmed, freer branching, with brighter red bracts and improved post-production keeping qualities compared to 'Lilo'. It is also less prone to "splitting".

1 Drawing Sheet

BACKGROUND OF THE NEW PLANT

This new poinsettia cultivar '529' originated as an induced sport of a seedling poinsettia known as 'F-23'. Cultivar 'F-23' was deemed to have desirable traits for commercial greenhouse production. It had attractive dark, but bright red flower bracts and contrasting dark green foliage. Most notable was its stiff, upright stems, a desirable trait for commercial pot plant production. Also, 'F-23' was relatively short, requiring little or no chemical growth retarding chemicals to achieve an acceptable commercial pot plant height. However, 'F-23' is not a self-branching cultivar. Cultivar '529' was then created by imparting self-branching to 'F-23' using the procedures set forth in U.S. Pat. No. 4,724,276. Cultivar '529' retains all of the desirable traits of 'F-23' and is self-branching.

There are other poinsettia cultivars with dark red bracts and dark green foliage, notably cultivar 'Lilo' U.S. Plant Pat. No. 6,694), the cultivar '529' most closely resembles. Cultivars 'F-23' and '529' differ from 'Lilo' in several aspects. Cultivars 'F-23' and '529' flower approximately 5 days earlier than 'Lilo'. They are shorter and have more rigid stems than 'Lilo'. Cultivar '529' branches more freely than 'Lilo'. The bract color, while similar to 'Lilo' is brighter with less bluish tones. Cultivar '529' is prone to premature flower initiation ("splitting") than 'Lilo'. In post-production environments '529', unlike 'Lilo', exhibits little or no bract edge burn, making it a longer-lasting cultivar with greater value for the consumer.

After cultivar '529' was induced, clones were produced by stem cuttings for further testing and evaluation. Successive generations of vegetative propagation demonstrated the distinctive characteristics of '529' hold true from generation to generation.

DESCRIPTION OF THE PHOTOGRAPHS

Poinsettia '529' is illustrated in the accompanying color photographs. The upper photo is a side view of one pinched, multi-branched plant in full flower. The lower photo is a top view of the same plant showing flower and bract formation.

DESCRIPTION OF THE PLANT

The following is a detailed description of this new poinsettia '529' as observed in my greenhouse in Encinitas, Calif., during December, 1990. I recorded observations from flowering plants, grown as 3 unpinched plants per pot. The pot was 14 cm. in diameter and 11 cm. in height. Comparisons were made under the same cultural conditions to cultivar 'F-23' from which '529' is derived, and to cultivar 'Lilo' (U.S. Plant Pat. No. 6,694) which has similar bract and foliage colors. Color designations are compared to the 1986 edition of R.H.S. Colour Chart, first published in 1966 by The Royal Horticultural Society, London, England.

THE PLANT

Origin: Sport of Seedling 'F-23'. The sport was induced by application of the procedures set forth in U.S. Pat. No. 4,724,276 to the seedling parent.

Classification:

*Botanic.*—*Euphorbia pulcherrima* Willd.

*Common name.*—Poinsettia.

*Cultivar name.*—'529'.

Form: Shrub.

Height: Medium.

Growth Habit: As a single stemmed plant, upright and stiff stemmed. I observed 3 plants in a pot with an overall height of 50 cm. and an overall width of 42 cm. By contrast, overall heights of 'F-23' and 'Lilo' were 50 cm. and 53 cm., respectively. The bract diameter of individual flowers was 30 cm.

Branching: Poinsettia '529' has self-branching traits. Axillary branches will develop and terminate in a flower without pinching. It may be desirable to pinch '529' and remove all terminal dominance. Then, 6–8 axillary branches usually will develop uniformly and at a faster rate. Cultivar 'F-23' does not have self-branching traits. Even after pinching, only 3–4 axillary branches develop on 'F-23'. 'Lilo', which does have self-branching traits, develops 5–6 axillary branches after pinching.

Growth rate: Rooting of stem cuttings occurs in 12–18 days under intermittent mist. The plant will flower in about eight weeks under continuous long night conditions and night temperatures of about 16–18 degrees C. Plants of '529' and 'F-23' were in "full flower" on Nov. 24, 1990, five days earlier than 'Lilo' which flowered on Nov. 29. Under long day conditions, '529' initiates flowering ("splits") at a greater leaf number than 'Lilo'. 'Lilo' normally "splits" after about 25 vegetative leaves. '529' initiates flowering (splits) only after 30–35 vegetative leaves have formed.

Foliage: The foliage is clean and uniformly dark green from bottom to top of the plant. The leaves are of medium size, leaf blades typically being 13–15 cm. long and 9–10 cm wide with leaf petioles 6–8 cm. long.

*Leaf shape.*—Typical leaves are ovate with obtuse bases and acuminate tips. Leaf margins are usually entire.

*Color.*—Upper side — Dark green, much darker than R.H.S. 147A. Under side — Green, darker than R.H.S. 147B.

*Retention.*—The foliage lasts extremely well even under low light intensities in the consumer's home.

Bracts: Generally there are 15–21 uniformly colored bracts of various sizes subtending the cyathia. The primary bracts have blades typically 14–16 cm. long and 8–9 cm. wide with petioles 2–4 cm. long.

*Shape.*—Primary bracts are mostly ovate with acute bases and acuminate tips. Secondary bracts are elliptic. Primary bracts are lobed with 1 or 2 indentations on either side of the bract. Secondary bracts have entire margins.

*Color.*—Upper side — Dark red, near R.H.S. 46B. Under side — Red, near R.H.S. 53C. The red bract color of '529' and 'F-23' is relatively brighter than 'Lilo'. 'Lilo' bracts have a more bluish tone.

Flowers: Generally, 15–21 cyathia (flowers) are present when the plant is in full bloom. Each cyathium is 6–7 mm long and 5–6 mm wide, green in color, and fringed with red at the distal end. Usually one, but occasionally two, yellow nectar cups tinged with red protrude from the side of each cyathium. The flower pedicel is also green and 4–5 mm in length. The stamens protruding from the cyathia are red and about 2.5 mm long. Anthers are bifurcate and pollen is yellow and copious. Stamens are numerous but only 4 to 6 are dehiscing at any one time. The pistils are dark red and about 2.5 mm in length and appear later than the stamens. The stigmas are trifurcate and dark red. No viable seed is formed without cross-pollination.

What is described is a dark red bracted, early flowering poinsettia named '529'. Cultivar '529' is a self-branching sport of a seedling poinsettia known as 'F-23'. Both cultivars '529' and 'F-23' have dark red bracts and dark green foliage similar to poinsettia cultivar 'Lilo' (U.S. Plant Pat. No. 6,694). However, '529' is stiffer stemmed, earlier flowering, shorter in height, branches more freely, has brighter red flower bracts, and is less prone to premature flower initiation and bract edge burn than 'Lilo'.

What is claimed is:

1. A new and distinct Poinsettia cultivar, substantially as herein shown and described, characterized by its stiff stems, short stature, dark red flower bracts, dark green foliage, strong branching habit and superior post-production keeping qualities.

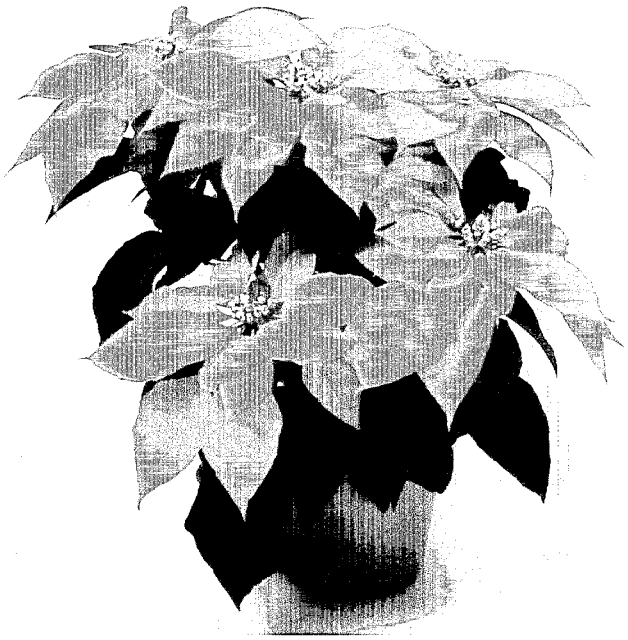
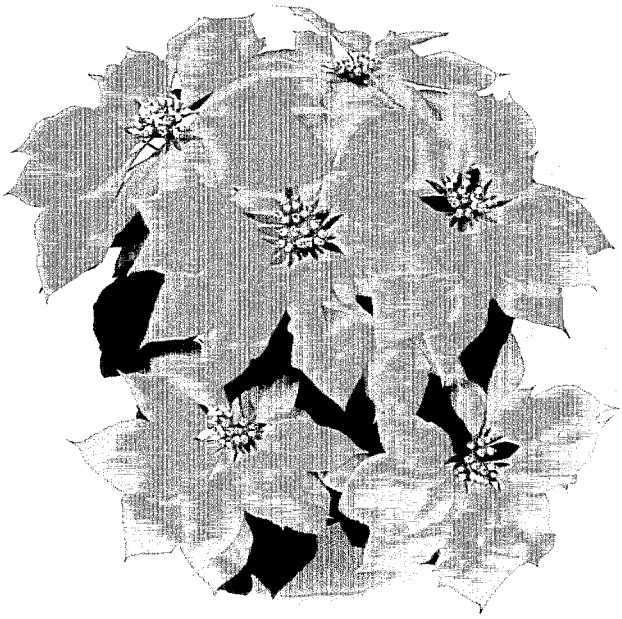

* * * * *